(12) United States Patent
Gensler

(10) Patent No.: US 6,870,376 B1
(45) Date of Patent: Mar. 22, 2005

(54) METHOD AND APPARATUS FOR DETERMINING PLANT WATER CONTENT

(76) Inventor: William G. Gensler, 4020 E. Coronado Dr., Tucson, AZ (US) 85718

( * ) Notice: Subject to any disclaimer, the term of this patent is extended or adjusted under 35 U.S.C. 154(b) by 31 days.

(21) Appl. No.: 10/664,661

(22) Filed: Sep. 20, 2003

(51) Int. Cl.[7] .............................................. G01R 27/26
(52) U.S. Cl. ...................................... 324/664; 324/663
(58) Field of Search ..................... 47/49; 73/73, 304 C, 73/304 R; 239/71; 324/658, 660, 662, 663, 664

(56) References Cited

U.S. PATENT DOCUMENTS

| | | | | |
|---|---|---|---|---|
| 3,771,548 | A | * 11/1973 | Rauchwerger | 137/392 |
| 3,967,198 | A | 6/1976 | Gensler | 324/72 |
| 4,021,733 | A | * 5/1977 | Green et al. | 324/665 |
| 4,114,090 | A | * 9/1978 | Poskitt | 324/667 |
| 4,952,868 | A | * 8/1990 | Scherer, III | 324/664 |
| 5,341,673 | A | * 8/1994 | Burns et al. | 73/73 |
| 5,479,104 | A | * 12/1995 | Cambell | 324/690 |
| 6,202,479 | B1 | * 3/2001 | Frybarger | 73/73 |
| 6,742,387 | B2 | * 6/2004 | Hamamoto et al. | 73/335.04 |

OTHER PUBLICATIONS

Gensler, W. 1999. Measuring and interpreting diurnal activity in the main stem of trees. In Tree Ring Analysis, Biological, Methodological and Environmental Aspects. R. Wimmer and R. E. Vetter eds. CABI Publishing. Wallingford, OX UK.

Lekas, T.M., R. G. MacDougall, D. A. MacLean and R. G. Thompson. 1990. Seasonal trends and effects of temperature and rainfall on stem electrical capacitance of spruce and fir trees. Can. J. For. Res. 20:970–977.

MacDougall, R. R., D. A. MacLean and R. G. Thompson. 1988. The use of electrical capacitance to determine the growth and vigor of spruce and fir trees and stands in New Brunswick. Can. J. For. Res. 18: 587–594.

MacDougall, R. G., R. G. Thompson and H. Piene. 1987. Stem electrical capacitance and resistance measurements as related to total foliar biomass of balsam fir trees. Can. J. For. Res. 17:1071–1074.

Fensom, D. 1959. The bio–electric potentials of plants and their functional significance. Can. J. Botany. 37: 1003–1026.

Geddes, L.A. 1972. Electrodes and the measurement of bio–electric events. Wiley Interscience, New York.

* cited by examiner

Primary Examiner—N. Le
Assistant Examiner—Walter Benson

(57) ABSTRACT

This invention is concerned with a method and plant-based apparatus to measure the water content within plants. A metallic surface is implanted in any orientation within the plant. The total area of this surface within the plant is measured with a mechanical caliper or equivalent. The wetted area of this surface is obtained by means of a measurement of electrical capacitance at the interface between the surface and water in the plant. Plant water content is equal to the ratio of measured capacitance to measured surface area within the plant. The apparatus functions as a "water dipstick" in the same manner as an "oil dipstick" in an automobile. The surface is normally implanted in the petiole in the early season and remains there until harvest. Water content readings are then used to set irrigation schedules. The full season chronology of water content readings can be extrapolated from site to site and season to season for optimization of agricultural practice.

3 Claims, 4 Drawing Sheets

METHOD AND APPARATUS FOR DETERMINING PLANT WATER CONTENT

FIELD OF THE INVENTION

This invention generally relates to botanical and agricultural measurements and more particularly to a method and apparatus that utilizes a plant-based mechanical measurement and a plant-based electrochemical measurement.

PRIOR ART I

U.S. Pat. No. 3,967,198. W. G. Gensler, Jun. 29, 1976.

The electrochemical circuit in this invention consists of a sensing electrode implanted in the tissue and a second electrode in the root environment. An electrical potential between the two wires attached to these electrodes is measured and used as a gauge for changes in metabolic activity of the plant and indirectly as a measure of plant water status. Electrical capacitance is not measured. The area of the surface of the sensing electrode implanted in the tissue is not measured.

During the period from 1976 to 1993, the electrical potential between a wire from the sensor surface in the plant and the second electrode in the soil was the sole measurement. The electrochemical characteristics of potential changes and the ation of the potential to plant characteristics were examined (Gensler, 1986, Gensler and Yan, 1988; Silva Diaz, Gensler and Sechaud, 1983; Gensler, 1990, Gensler, 1994).

During the period from 1993 to 2002, measurement of electrical capacitance between the two wires from the sensing and second electrodes was used as a measure of water content (Gensler, 1999). The method consists of a sequence of capacitance measurements. The first measurement in the sequence was a capacitance measured under a high soil moisture level, namely, field water saturation. This became the base capacitance value. The assumption was made that the plant would come into equilibrium with the soil and reach a similar saturated value. Subsequent measurements of capacitance at soil moisture conditions less than field saturation would result in a new equilibrium between plant and soil. The assumption was made that this new equilibrium would be at a lower plant water content. A measure of water content was formed by using the base capacitance measurement and any subsequent capacitance measurement.

There was no measurement made of the area of the sensor inside the plant. All water content values were expressed as percent water content using the value of capacitance measured under field saturation of the soil as a base value. The base capacitance (or capacitance at soil field water saturation) was arbitrary and decided upon by visual appraisal of field conditions. Percent water content values were relative, that is, they were compared to an arbitrary soil-based level. Under the assumption that a maximum soil water content led to a maximum plant water content, the water content varied from 100% down to zero.

This method, termed "The Percent Method," worked well under conditions wherein the plants would drydown and maintain water content levels less than field saturation. It effectively quantified drydown within a single season at an individual site.

The Percent Method surmounted the serious problem which arises from the difference in the diameters of the stems or petioles within a given group. The problem is as follows: Assume a sensor is implanted in a large diameter petiole in a plant and a small diameter petiole in an adjacent plant. Assuming the soil water content is the same in both plants the large petiole would yield a larger value of capacitance than the smaller petiole. To take this into account, each sensor had its own base value of capacitance taken at the same time. Percent values were formed on an individual basis. The individual percent values were then averaged to yield an average percent value of water content for the entire group.

The Percent Method had the disadvantage that the base value was arbitrary and it was not possible to extrapolate from site to site and from season to season. The base value was selected visually within each site and within each season.

A further and cardinal disadvantage of The Percent Method was the discovery during the 2002 growing season that imbibition (water uptake) by the plant was not maximally set by the conditions in the soil. Plants growing under favorable soil water conditions would hyperimbibe. They would take in water in excess of magnitudes set by soil water content. The presence of hyperimbibition made the selection of a base value of wetted sensor surface area inside the plant completely relative. Soil moisture at the field saturation level was not a valid base value. This was a cornerstone of The Percent Method. Extrapolation from field to field and season to season was not possible. Results were limited to an individual field in a single season. This negated any possibility of using the results from one season to the next in an attempt to optimize irrigation scheduling.

These two problems necessitated a new approach to the measurement of plant water content.

PRIOR ART II

Electrical measurements of plant tissue were the subject of a long line of research largely beginning with Fenson (1958). The apparatus was consistent in that two identical stainless steel electrodes (essentially nails) were driven in the trunks of trees in an attempt to quantify the characteristics of the volume of tissue (referred to as the bulk tissue) between the two electrodes (see FIG. 1 in MacDougall, Thompson and Piene, 1987; MacDougall, MacLean and Thompson, 1988; and Lekas, 1990). The two common parameters in these measurements are the bulk tissue electrical resistance and the bulk tissue electrical capacitance. The experimental procedure consisted of the application of a sinusoidal electrical potential between the electrodes thereby causing an electrical current to flow through the tissue from one electrode to another. The ratio of potential to current leads to an electrical impedance which varies with frequency. At any given frequency the impedance can be described in terms of a simple parallel resistor and capacitor. Results were reported in terms of capacitance at picofarad levels.

In the approach described immediately above, the electrochemical circuit consists of two electrodes located in the tissue. Both electrode interfaces are biological, that is, the interface is comprised of an electrode and tissue. The volume of the tissue embodied in the circuit path is roughly defined as the distance between the two electrodes over many path lengths. The term "capacitance" is a mathematical construct arising from changes in the ratio between applied potential and resulting current as the frequency of the potential source is varied. Capacitance is not a unique value but varies as a function of frequency (Geddes, 1972). This introduces an arbitrariness in the value of capacitance. Furthermore, capacitance is a bulk tissue characteristic, that is, a characteristic set by the volume of cell membranes and transport tissue between the electrodes. This same focus on bulk tissue capacitance has existed in still earlier work (Marsh, G., 1944). There is no direct correlation of bulk water content to bulk tissue capacitance in these approaches.

The equivalent parallel resistance and capacitance values obtained are a complex mixture of interfacial and bulk tissue characteristics, as opposed to the interfacial capacitance in this invention. There was no attempt in this research to define or report on a variable such as capacitance per unit length of an electrode within the tissue. The surface area of the electrodes was not reported.

In this prior art, capacitance was viewed as a means of determining bulk tissue characteristics. As will be seen below, in the apparatus of this invention capacitance is simply a means to obtain a linearly proportional measure of the amount of wetted area of an implanted surface. This difference shows up very significantly in how capacitance is reported in this prior art and in this invention. In this prior art, capacitance is reported in terms of farads. In this invention capacitance is stated as part of an output variable in terms of farads/mm, essentially, wetted area per unit total area.

PRIOR ART III

The characteristics of an electrode-electrolyte interface have been studied most extensively as this is the foundation of the entire subject of electrochemistry (Bard and Faulkner, 1980). Biomedical applications of electrode-electroyte interfaces have been reviewed by Geddes (1972). A summary of the interfacial capacitance values using a variety of electrode material-electrolyte combinations is given in Geddes, FIGS. 1–6. These values are obtained when an alternating potential is applied to the interface and the potential and resultant current measured at varying frequencies. The capacitance is derived as one component of the impedance of the interface. The experimental procedure to obtain these results is to totally immerse the electrode in the electrolyte and make the measurements. The wetted surface area is fixed. The procedure is in-vitro. Capacitance as a function of variable wetted surface area of the electrode is not a consideration or part of the measurement procedure. This is in contrast to this invention in which the wetted area of the interface is an essential measurement. This variation in area is an integral part of the invention. The physical extent of the layers of opposite charge that make up the capacitor is a principal measurement in the invention. The procedure is in-vivo.

There have been numerous liquid level sensors commercially manufactured utilizing a "water dipstick." These are level sensors as opposed to content sensors. This distinction is more than semantics. Level sensors require that the surface has a fixed gravitational orientation. For example, the level of water in a tank requires that the dipstick be oriented from the top of the tank to the bottom. In this invention, no such limitation is imposed. The sensor surface can function at any gravitational orientation. Water content itself in a plant is not a function of gravitational orientation or even location with the plant structure.

There are soil water content apparatus which work in any orientation that employ a radio frequency generator within a tube (approximately 10 centimeters in diameter) placed in a hole in the soil. A radio frequency is emitted from the tube and a radio frequency receiver within the tube receives a part of the radio frequency energy depending on the amount of water content in the region around the tube. This apparatus does not make any measurement of the area of the wetted surface of the tube. The total area of the tube containing the electronics is also not part of the measurement. This equipment has never been placed within a plant. Surface phenomenon are not within the scope of this apparatus. By contrast, in this invention the sensor surface is placed within the plant and the measurements of total area and wetted area are necessary parts of the invention.

OBJECTS AND ADVANTAGES

The method and apparatus of measurement of total sensor surface area and capacitance in this invention solves all three problems encountered in the previous method of measuring plant water content employing only a capacitance measurement and a visual appraisal of soil moisture content. The apparatus and method takes into account hyperimbibition. It yields a water content value that can be compared from site to site and season to season. It takes into account difference in petiole or stem diameters.

The combined measurements take into account hyperimbibition insofar as the presence of increased water in the tissue is manifest in the presence of greater wetted surface at a given sensor length within the tissue. Analysis of the diameter values of plants that have hyperimbibed indicates that the increased water content results in a greater proportion of the surface area of the sensor inside the plant that is wetted at the same total sensor surface area. The petiole does not physically swell. A volume inside the plant that was formerly occupied by air becomes occupied by water.

The variability in petiole or stem diameter is taken into account by the measurement of the area of each individual sensor. The ratio described above is applied to each sensor within the group and the group average water content is the average of the ratio of capacitance to area of each individual sensor. In normal cultural practice under field conditions, fifteen sensors are used with a single second electrode.

The ability to extrapolate or compare the water content between sites and from season to season is possible because the measured variables are dependent on the plant itself. For example, a petiole thickness of three millimeters one season is the same as a petiole thickness of three millimeters the next season. The sensor is implanted early in the season and remains within the plant until harvest depending on the anatomy of the plant. This long duration monitoring permits observation of the manner in which the plant responds to changing soil and environmental conditions. Irrigation schedules are adjusted accordingly.

The water content in this invention is an absolute number. For example, in the petioles of wine grapes a scale has been empirically formed of favorable petiole water content values at harvest: syrah petioles, 20 Nfd/mm; merlot petioles, 30 Nfd/mm and chardonnay petioles, 40 Nfd/mm. This scale is valid from season to season and site to site. These numbers are derived from the plant alone.

FIGURES

REFERENCE NUMERALS IN FIGURES

1 Sensor Surface
2 Plant

3 First Wire Connected to the Sensor Surface
5 Second Wire Connected to the Second Electrode
6 Length of the Sensor Surface Within the Plant
7 Second Electrode
8 Root Environment
9 Petiole
10 Leaf Blade
12 A Water Cluster on the Sensor Surface Within the Petiole
14 Sensor Surface Within the Petiole

DESCRIPTION

Figure 1:
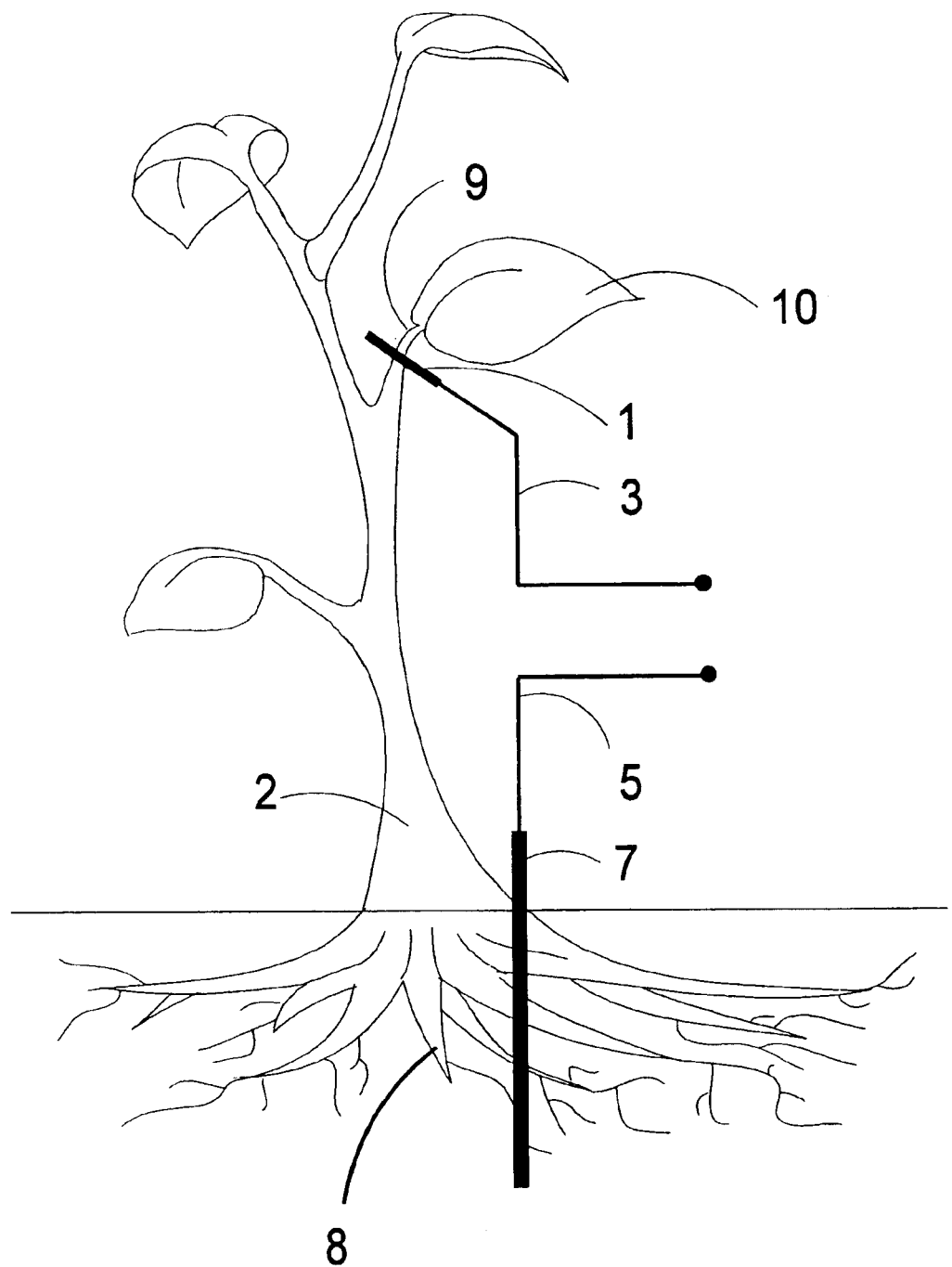
FIG. 1 is an illustration of the sensor surface in the petiole of a plant and the second electrode in the root environment.
Figure 2:
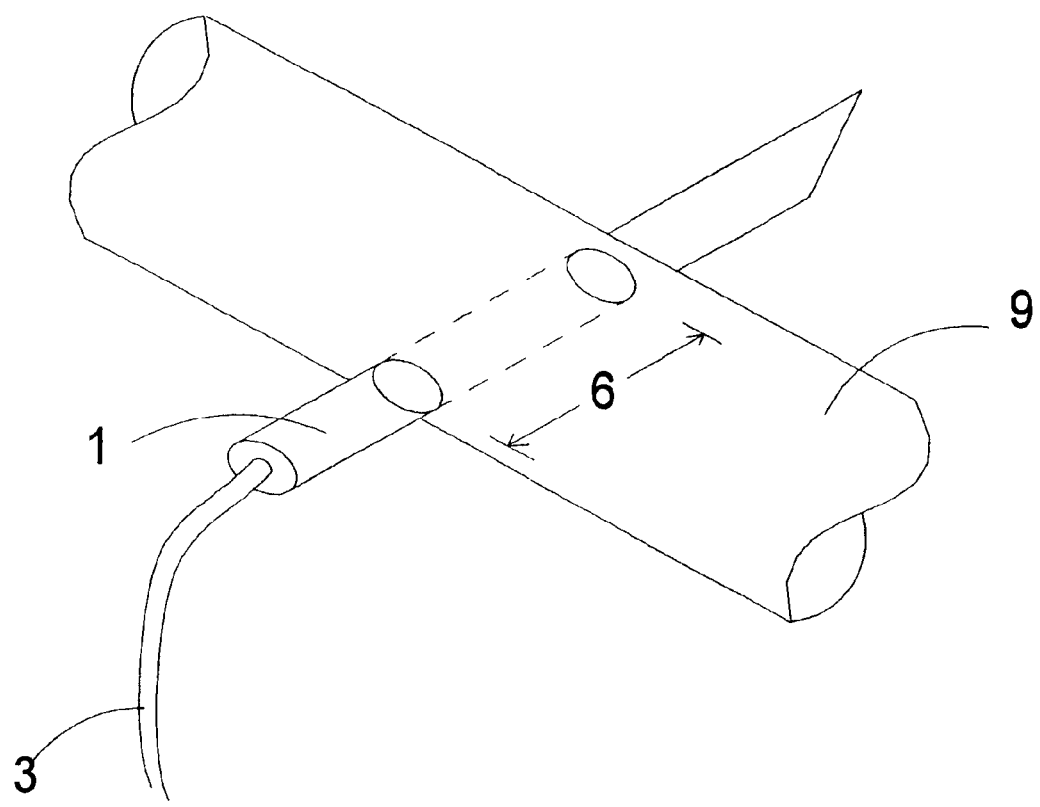
FIG. 2 is an expanded view of the sensor surface in a petiole and the measured length of the sensor within the petiole.

FIG. 1 shows the apparatus for the basic measurement of plant water status. A sensor surface 1 is placed within the plant 2 and a second electrode 7 is placed in the root environment. A first wire 3 is connected to the sensor surface. A second wire 7 is connected to the second electrode. FIG. 2 shows an expanded view of the sensor surface inside the plant. In this case the location within the plant is the petiole of a leaf. The sensor surface goes into one side of the petiole and out the other side of the petiole. The electrical capacitance between the ends of the two wires is measured. The total sensor surface length 6 within the plant is obtained with a caliper or equivalent.

In terms of the measured variables, water content for a cylindrical sensor becomes $$\text{Water Content} = \frac{\text{Electrical Capacitance}}{\text{Length of the Sensor Surface within the Plant}} \quad (1)$$

The units of water content are farads/meter. In terms of the values commonly encountered under field conditions, the units are Nanofards/millimeter.

Figure 3A:
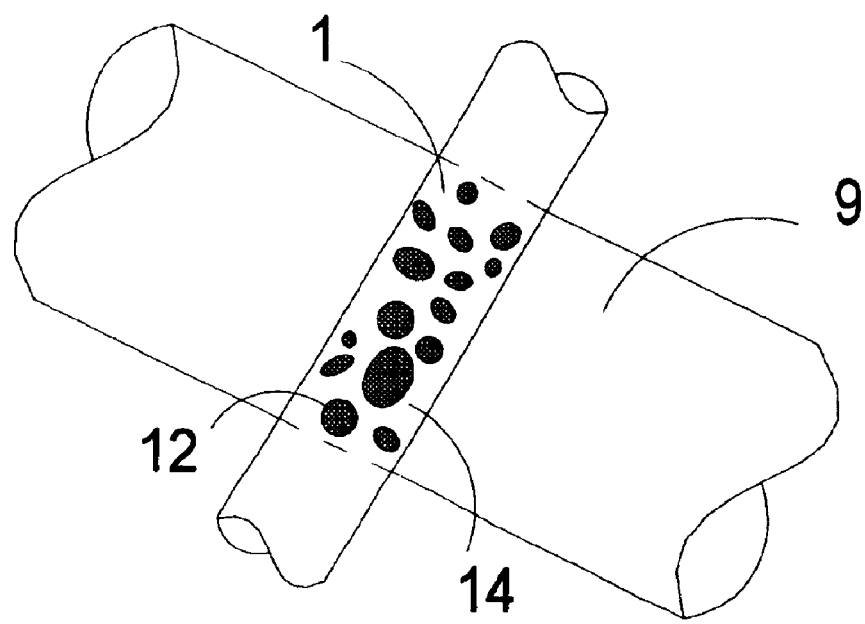
FIG. 3A is a schematic view of water clusters wetting the sensor surface at high water content values.
Figure 3B:
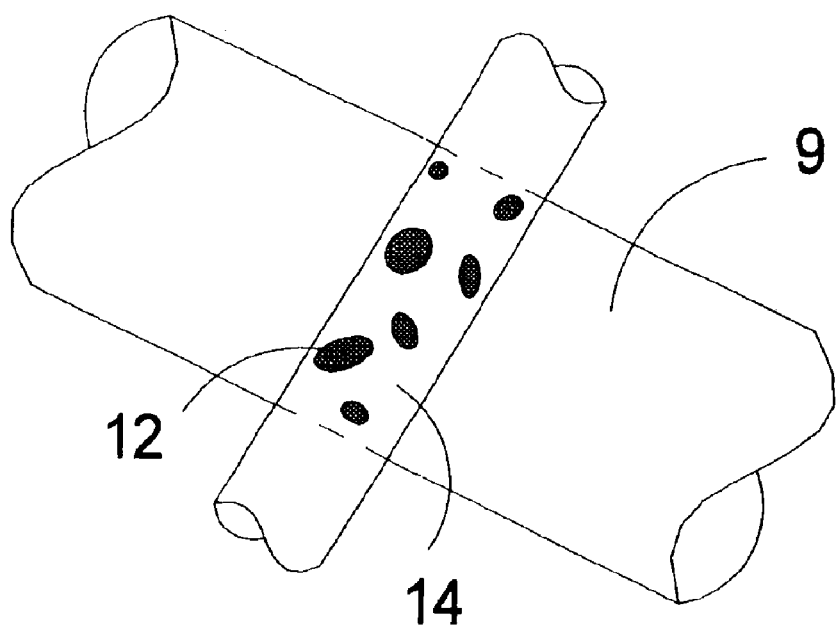
FIG. 3B is a schematic view of water clusters wetting the sensor surface at low water content values.

FIGS. 3A and 3B show the sensor surface with clusters of water on the surface under high water content conditions and low water content conditions, respectively. As the water content of the plant increases, the wetted area 12 on the sensor surface 14 increases and vice versa.

The question that must be addressed is what relation does electrical capacitance have with these changes in wetted surface area on the sensor surface. How can electrical capacitance give an indication of the change in the extent of wetted area shown in FIG. 3A and FIG. 3B?

To answer this question one must examine the characteristics of water on the surface of a noble metal surface. Water on the surface of a noble metal contains dissolved oxygen. This oxygen adsorbs and ionizes on the surface of the noble metal sensor (Hoare, 1968). Ionized oxygen forms one layer of charge of an electrical capacitor. The second layer of charge consists of electrons in the metal. These two opposing charge layers form an electrical capacitor. The magnitude of the capacitor is a function of the wetted surface area of the filament in the tissue, the distance between the charge layers and the dielectric constant of the material between the charge layers. In this case the distance between the charge layers is fixed by virtue of the fact that water resides on the sensor surface. The dielectric is water. As the wetted area changes, the electrical capacitance of the interface changes.

In conclusion, the value of interfacial capacitance of the sensor surface-wetted area gives a measure of the extent of this wetted area.

This theory can be verified by the following simple experimental procedure. A cup is filled with tap water. A sensor surface (in this case a filament of noble metal 150 micrometers in diameter) is suspended above the surface of the water. A second electrode is immersed in a cup. The second electrode is a brass rod, 2.42 millimeters in diameter, immersed to a depth of 78 millimeters. The filament is gradually lowered into the water. The capacitance is measured between a first wire attached to the sensor surface and a second wire attached to the second electrode in the same manner as shown in FIG. 1. This situation matches the situation in the plant except the root environment is totally liquid in this calibration setup and the sensor surface is progressively covered with water.

Figure 4:
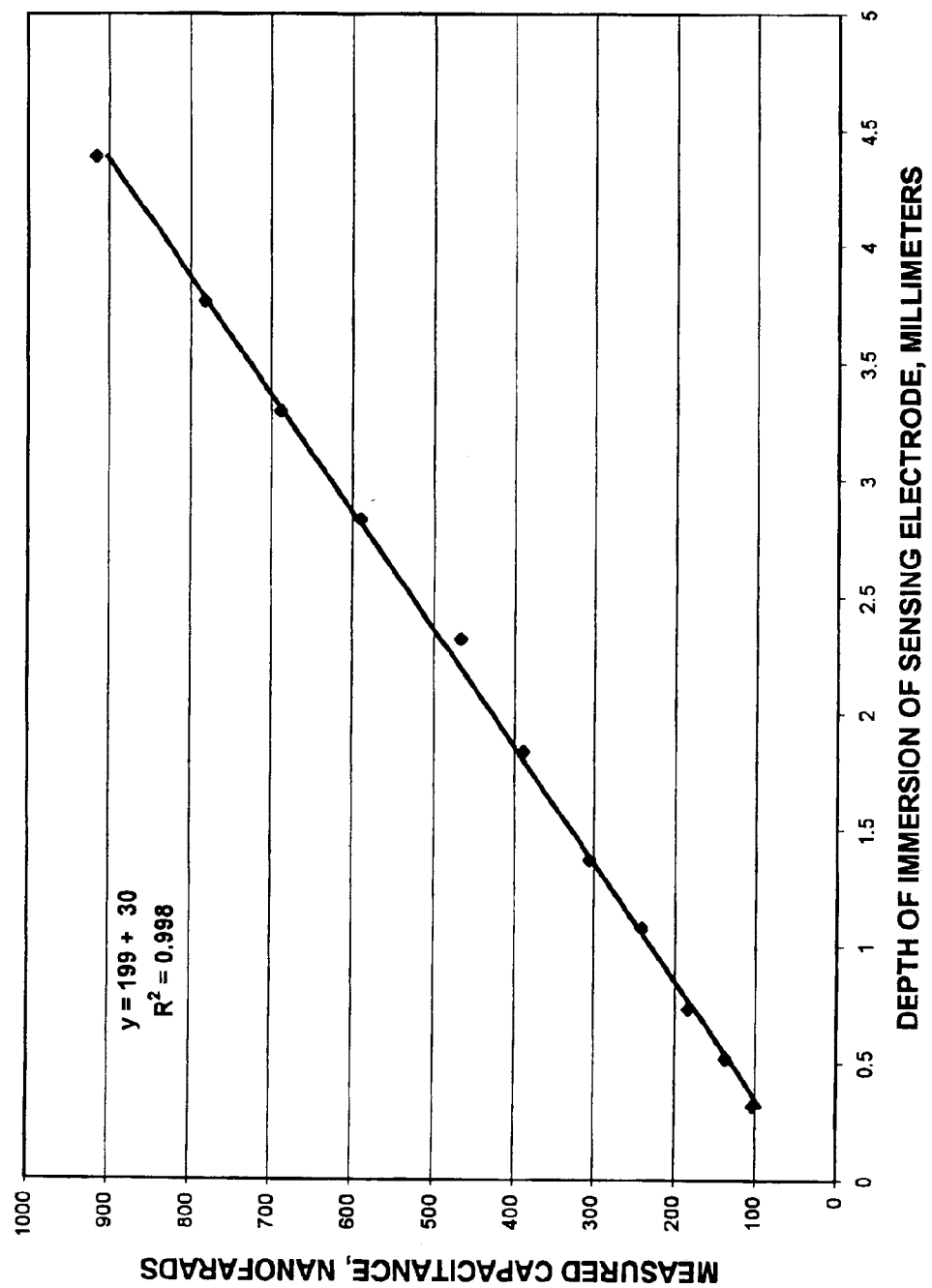
FIG. 4 is a calibration curve of the measured capacitance as a cylindrical sensor is gradually immersed in a cup containing tap water and a second electrode.

FIG. 4 illustrates the measured capacitance as the sensor surface is immersed deeper and deeper into the water. The increase in wetted area results in a linear increase in capacitance. In other words, as the wetted area of the sensor surface increases, the capacitance measured between the two wires increases. This is because the layers of charge in the water and metal increase in area. A linear least squares fit of the data points yields the relation:

$$y = 199*x + 30$$

where y is the measured capacitance in nanofarads and x is the depth of immersion in millimeters. This equation states that the capacitance increases 199 nanofarads for each increase in one millimeter in the depth of immersion. By extrapolating to zero immersion, the capacitance is 30 nanofarads. This is the intercept on the vertical axis of the straight line fit over the data points. This intercept is the capacitance in the remainder of the circuit pathway from the water in the cup through the water-second electrode interface and back through the second electrode wire. This capacitance is a constant value. The measured capacitance is the total capacitance in the path consisting of this constant value of capacitance plus a variable value of capacitance depending on the water content of the plant.

The next question to address is how the ratio on the right side of Eqn. 1 can be interpreted in terms of a "water dipstick." First substitute Eqn 2 in Eqn. 1, $$\text{Water Content} = \frac{199*\text{wetted length of sensor} + 30}{\text{Length of the Sensor Surface within the Plant}} \quad (3)$$

Convert length variables to area variables assuming a cylindrical sensor surface.

$$\text{Water Content} = \frac{(199*\text{wetted length of sensor surface} + 30)*\text{Diameter}*\prod}{\text{Length of the Sensor Surface within the Plant}*\text{Diameter}*\prod} \quad (4)$$

$$\text{Water Content} = \frac{199*\text{wetted area}}{\text{total sensor surface area}} + \frac{30*\text{Diameter}*\Pi}{\text{total sensor surface area}} \quad (5)$$

Simplifying the terms $$\text{Water Contenet} = K_1 * \frac{\text{wetted area of the sensor surface}}{\text{total area of the sensor surface}} + K_2 \quad (6)$$

where $K_1$ is 199 nanofarads/mm and $K_2$ is 30/length of the sensor surface within the plant in millimeters.

Eqn 6 indicates the ratio of the measured capacitance over the measured length of the sensor surface within the plant is proportional to a ratio of the wetted area of the sensor surface to the total area of the sensor surface plus an additive constant. In other words, a water dipstick plus an additive constant. The additive constant is usually neglected.

Based on field observations at over forty production agriculture sites in the summer of 2003, the variable value of capacitance per unit length at the sensor surface varies between about 20 to 140 nanofarads/mm. This indicates plants with a very high water content will not reach the maximum level of 199 nanofarads/millimeter. In other words, even at very high water content levels there is a substantial part of the surface area of the sensor surface covered with air. The range of immersion depth in FIG. 4 matches the range of diameters of the stems, petioles and peduncles encountered in normal agricultural practice, that is, from two to six millimeters.

Further verification of the two charge layer model of the interface between the sensor surface and water can be gained by calculating the distance between the two charge layers based on values in Eqn. 2. For a capacitor consisting of two parallel plates separated by a dielectric material (Boylstad and Nashelsky, 1977, page 51)

$$\text{Capacitance} = \frac{\text{Area of a plate} * \text{Dielectric Value of the Water}}{\text{Distance Between the Plates}} \quad (7)$$

$$199 * 10e - 9 = \frac{(1 * 150 * 10e - 6 * 3.14) * (80 * 8.85 * 10e - 12)}{\text{Distance Between the Plates}}$$

Where 80 is the relative permittivity and 8.85*10e-12 is the permittivity of air (Bard, 1980). The distance between the plates is 1.67 nanometers. This indicates the charge layers are separated by atomic dimensions and verifies that the measured changes in capacitance arise at the sensor surface-water interface.

In this calibration setup, the second electrode has a constant surface area of 592 millimeters squared, a capacitance of 30 nanometers and a capacitance per unit area of 0.05 nanofarads/millimeter squared. By contrast, the sensor surface has a capacitance per unit area of 422 nanofarads/millimeter squared. This is a difference of over 8000 to 1. This indicates the ratio of the measured capacitance/measured area is essentially the capacitance/unit area of the sensor surface plus an additive constant. In cultural practice, the additive constant can be neglected. The reason for this is that in production agriculture plants with water content levels down so low as to make the additive constant significant would be not suitable for harvest or commercial sale.

CONCLUSIONS, RAMIFICATIONS AND SCOPE OF INVENTION

The water content within a plant can be determined by implanting a sensor surface within a plant and then measuring the total area of the sensor surface and the electrical capacitance. As the water content of the plant increases and decreases, the electrical capacitance increases and decreases. The ratio of electrical capacitance to total length of the sensor surface within the plant functions in the same manner as a water dipstick. This dipstick functions in any gravitational orientation and also in any change in gravitational orientation. The latter would occur as movement of the leaf blade in the wind or growth causes shifts in the orientation of the petiole.

Both capacitance and length measurements are plant-based. Soil and environmental influences are integrated by the plant and yield the resultant level of water content and a resultant ratio. Weather conditions such as high temperatures causes dehydration, irrigation causes rehydration. The water content changes accordingly.

The water content values can be applied from site to site and from season to season. It is intrinsic to the plant. A merlot wine grapevine with a petiole water content value of 30 Nfd/mm at harvest one year can be adjusted to 40 Nfd/mm the following year if grape quality dictates a higher level.

The apparatus can be applied to any plant type in which a measurement of total area and wetted area of the implanted surface can be made.

The total area of the surface within the plant can be measured two ways: by implanting the surface within the plant and them measuring the extent of the implanted surface within the plant. Alternately, the total area can be measured before the surface is implanted and then implanting the surface such that this pre-measured total surface lies within the plant. The first method is useful in implants in which the surface enters and exits from the plant such as in petioles. The second method is useful in implants in which the surface enters but does not exit out the other side. This is the preferred method in fruit with skin such that penetration of the fruit through the calyx does not destroy the integrity of the fruit, but exit out the skin would destroy the integrity of the fruit.

The sensor surface itself has several embodiments. A cylindrical shape is the simplest form because the entire surface of the sensor is uniformly sensitive, it is mechanically the most rigid shape and is manufactured most readily. In the case of an implant which enters the tissue but does not protrude out of the tissue, the filament can be bent such that a known length is implanted within the tissue. This is required in applications such as implants into grapes wherein puncture of the skin would destroy the integrity of the grape. The second electrode also has many embodiments. Its shape, size and material will vary. In order to maintain a large ratio between interfacial capacitance of the sensor surface versus the second electrode, it is best to use a sensor surface material which has a high level of oxygen adsorption and ionization. By contrast, the second electrode material should have a minimal level of oxygen adsorption and ionization. This is not essential, but will yield the maximum resolution and range. It is best to use a second electrode with a large surface area compared to the surface area of the sensor surface. This will minimize any interfacial resistance.

While there have been illustrated and described various embodiments of the present invention, it will be apparent to those skilled in the art that modification thereof will occur to those skilled in the art. It is intended in the appended claims to cover all such changes and modifications that fall within the true scope and spirit of the present invention.

I claim:

1. A method for measuring the water content within a plant comprising the steps of:

placing a sensor electrode in any gravitation orientation implanted within said plant, placing a second electrode in a root environment, measuring the area of said sensor electrode implanted within said plant, measuring the electrical capacitance between a first wire connected to said sensor electrode and a second wire connected to said second electrode in said root environment, forming a ratio of said electrical capacitance to said area of said electrode surface for determining water content.

2. Apparatus for measuring the water content within a plant comprising:

sensor electrode means for implanting within said plant, second electrode for making contact with a root environment, first wire connected to said sensor electrode, second wire connected to said second electrode, means coupled to said first wire and said second wire for measuring the electrical capacitance generated therebetween by said plant, means for measuring area of said sensor electrode implanted within said plant, means for determining water content by forming a ratio of said electrical capacitance to said area of said electrode surface.

3. Apparatus as recited in claim 2 further including a plurality of sensor electrode means and means interposed between each of said sensor electrodes and said measuring means for selectively connecting each one of the said sensor electrodes to said measuring means.

* * * * *